US00PP35754P2

(12) United States Plant Patent
Read

(10) Patent No.: US PP35,754 P2
(45) Date of Patent: Apr. 16, 2024

(54) ***LEUCANTHEMUM* PLANT NAMED 'REAL WINNER'**

(50) Latin Name: ***Leucanthemum* x *superbum***
Varietal Denomination: Real Winner

(71) Applicant: Charles Richard Read, Bognor Regis (GB)

(72) Inventor: Charles Richard Read, Bognor Regis (GB)

( * ) Notice: Subject to any disclaimer, the term of this patent is extended or adjusted under 35 U.S.C. 154(b) by 0 days.

(21) Appl. No.: 18/183,791

(22) Filed: Mar. 14, 2023

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
CPC ..... A01H 5/02; A01H 5/00; A01H 6/14
See application file for complete search history.

(56) References Cited

U.S. PATENT DOCUMENTS

PP23,873 P2 * 9/2013 Lintott ..... A01H 5/02
Plt./285

* cited by examiner

*Primary Examiner* — June Hwu
(74) *Attorney, Agent, or Firm* — Weatherly IP Solutions, LLC; James M. Weatherly

(57) ABSTRACT

A new cultivar of *Leucanthemum* plant named 'Real Winner' that is distinguishable by its clumping basal-branching and upright plant habit and inflorescences consisting of pure white ray florets surrounding deep yellow disc florets. The ray florets of 'Real Winner' are arranged in two concentric whorls and appear fringed, being divided fan-like into three to five free narrow lobes. Flowering of 'Real Winner' commences in late June and continues until October. 'Real Winner' is hardy in USDA Zone 5.

2 Drawing Sheets

Genus and species: *Leucanthemum* x *superbum*.
Variety denomination: 'Real Winner'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Winner'.

*Leucanthemum* is a genus within the family Asteraceae in which the commonly referred to "flower" is botanically the inflorescence which is comprised of outer showy ray florets surrounding smaller disc florets.

'Real Winner' arose and was selected from an ongoing breeding program which is conducted by the inventor at the inventor's nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Winner' is a seedling selection that resulted from the controlled pollination of a single plant of the inventor's proprietary *Leucanthemum* seedling code L1028-8 (unreleased and unpatented) as the female parent, using pollen from a single plant of the inventor's proprietary *Leucanthemum* seedling code L1304-13 (unreleased and unpatented)

as the male parent. The inventor selected 'Real Winner' in 2018 for its strong growth habit and profuse flowering with flowers consisting of pure white fringed ray florets. 'Real Winner' was first asexually propagated by the inventor in West Sussex, United Kingdom in 2019 using the method of vegetative division and subsequently by basal shoot cuttings. Since that time under careful observation 'Real Winner' has been determined uniform, stable and true to type in subsequent generations of asexual propagation.

SUMMARY

The following traits have been repeatedly observed and represent the distinguishing characteristics of 'Real Winner'. In combination, these traits set 'Real Winner' apart from all other existing varieties of *Leucanthemum* known to the inventor. 'Real Winner' has not been tested under all possible conditions and phenotypic differences may be observed with variations in environmental, climatic, and cultural conditions, however, without any variance in genotype.

1. 'Real Winner' exhibits a clumping basal-branching and upright plant habit.
2. A fully expanded inflorescence of 'Real Winner' is 9 cm in diameter and is comprised of ray florets arranged around a central disc.
3. The ray florets of 'Real Winner' are arranged in two concentric whorls.
4. The ray florets of 'Real Winner' are pure white in color.
5. The petals of the ray florets of 'Real Winner' are appear fringed, being divided fan-like into three to five free narrow lobes.

6. The inflorescences of 'Real Winner' are carried on strong stiff stems.
7. Flowering of 'Real Winner' commences in late June and continues until October.
8. After one year of growth in a 2 gallon container, or planted in the ground, a plant of 'Real Winner' is 45-50 cm in height and 35- 0 cm in width.
9. 'Real Winner' is hardy in USDA Zone 5 (−20° F. or −28° C.).

BRIEF DESCRIPTION OF THE PHOTOGRAPHS

The accompanying color photographs were taken in July 2022 in Santa Barbara, California. The photographs illustrate the overall appearance of 'Real Winner' showing the color of foliage and inflorescence as true as is reasonably possible to obtain in color reproductions of this type. The illustrated plants had been grown in 2-gallon containers out of doors, without any pruning or use of chemical growth regulators. The colors in the photographs may differ from color values cited in the detailed botanical description, which accurately describe the actual color of 'Real Winner'.

BOTANICAL DESCRIPTION OF THE PLANT

Figure 1:
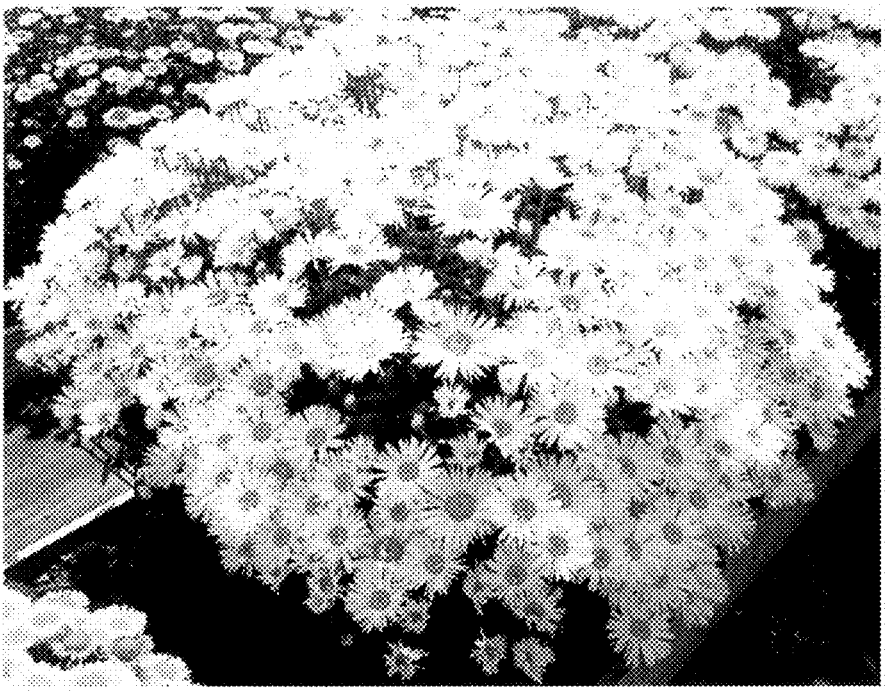
FIG. 1 illustrates, in the foreground, an eighteen month old plant of 'Real Winner' (from initial cuttings) which is growing outdoors in a 2-gallon container.
Figure 2:
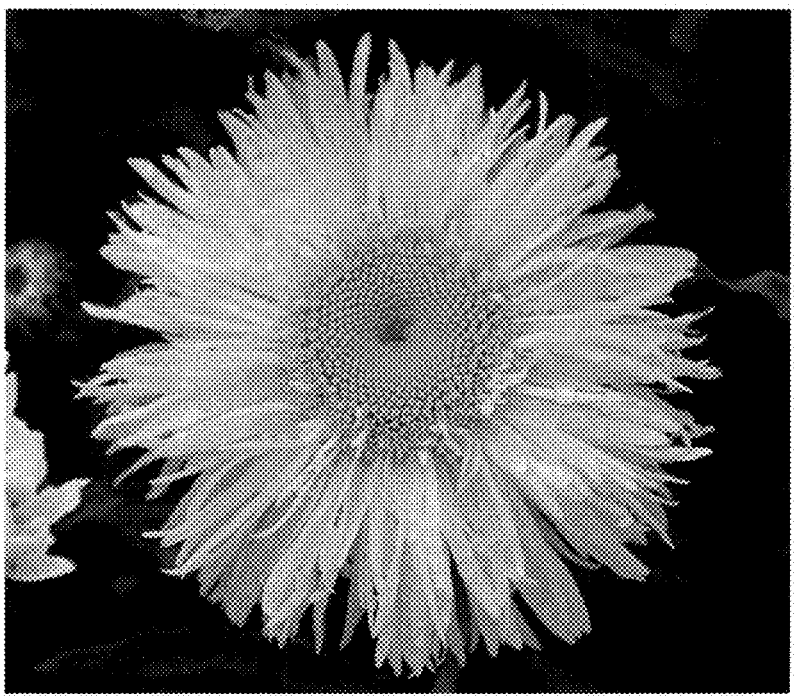
FIG. 2 depicts a close-up view of the inflorescences of 'Real Winner'.

The following is a detailed botanical description of the new cultivar 'Real Winner'. Observations, measurements, values and comparisons were collected in Santa Barbara, California during August 2022, from an eighteen month old plant growing outdoors in 2-gallon container. Color determinations are made in accordance with The 2007 Royal Horticultural Society Colour Chart from London, England, except where general color terms of ordinary dictionary significance are used.

Botanical classification:

*Family*.—Asteraceae (formerly Compositae).

*Genus*.—*Leucanthemum*.

*Species*.—X *superbum*.

Denomination.—'Real Winner'.

*Common name*.—Shasta daisy.

*Habit*.—Vigorous basal-branching upright growth habit.

*Commercial category*.—Perennial.

*Use*.—For garden and landscape.

*Suggested commercial container size*.—4-inch, 1 gallon, 2-gallon containers.

*Parentage*.—*Leucanthemum* x *superbum* 'Real Winner' is a seedling selection resulting from the controlled cross-pollination of the following parents. Male parent: Inventor's proprietary *Leucanthemum* seedling code L1304-13. Female parent: Inventor's proprietary *Leucanthemum* seedling code L1028-8.

*Propagation method*.—Basal shoot cuttings and division.

*Rooting system*.—Fine and fibrous.

*Vigor*.—Vigorous

*Time to develop roots* (*range*).—14 to 20 days are needed for an initial cutting to develop roots.

*Temperature to develop roots* (*range*).—The recommended air temperature is 20° C. to 21° C.

*Crop time* (*range*).—7 to 8 months to produce a flowering plant in a 1-gallon container starting from a rooted cutting. 10 months to produce a full plant in a 2-gallon container.

*Plant dimensions* (*eighteen months*).—45-50 cm in height and 35-40 cm in width.

*Cultural requirements*.—Grow in full sun and rich, moist moderately fertile well-draining soil.

*Pest or disease resistance and susceptibility*.—No specific disease or pest resistance or susceptibility has been observed or is known to the inventor.

*Hardiness*.—USDA Zone 5.

Stem:

*Branching*.—Basal, all stems bear terminal inflorescence.

*Dimensions*.—20 cm in length, 6 mm in diameter at soil surface.

*Shape*.—Terete, longitudinal ridges.

*Color*.—145B between ridges, ridges color 143A.

*Strength*.—Moderately stiff.

*Surface*.—Smooth, glabrous.

Foliage (cauline leaves and basal leaves, except dimensions):

*Type* (*division*).—Simple.

*Arrangement*.—Alternate.

*Internode length* (*range*).—1.5 cm to 2.5 cm.

*Margin*.—Dentate; 5-8 teeth per leaf edge, projecting 1.5-2.0 mm, spaced between 7 mm and 18 mm apart, pointing towards leaf apex.

*Apex*.—Acute.

*Base*.—Attenuate.

*Leaf attachment*.—Sessile.

*Leaf color* (*both surfaces*).—N137D.

*Leaf shape*.—Lanceolate, occasionally falcate.

*Leaf dimensions* (*cauline leaves*).—85 mm in length, 18 mm in width.

*Leaf dimensions* (*basal leaves*).—Up to 125 mm in length, 35 mm in width.

*Leaf venation*.—Very faintly pinnate.

*Vein color* (*both surfaces*).—As leaf N137B except adaxial midrib color 144B.

*Leaf surface* (*adaxial surface*).—Lightly puberulent, semi-glossy.

*Leaf surface* (*abaxial surface*).—Lightly puberulent, matte.

Inflorescence:

*Inflorescence type*.—Capitulum, flattened dome, consisting of ray florets and disc florets.

*Inflorescence quantity* (*average*).—30 (including buds).

*Inflorescence diameter* (*fully opened*).—9 cm.

*Inflorescence depth*.—2.5 cm.

*Receptacle dimensions*.—24 mm in diameter, 7 mm in height.

*Receptacle color*.—138B.

*Inflorescence aspect*.—Upright.

*Inflorescence colors* (*when fully developed*).—Ray florets: NN155D. Central disc: 14A.

*Fragrance*.—Slightly musty.

*Blooming season*.—Late June to October.

*Lastingness of inflorescence* (*range*).—10 to 14 days on the plant; ray florets are persistent.

Bud:

*Bud dimensions* (*immediately prior to ray flower appearance*).—9 mm in height and 17 mm in diameter.

*Bud shape*.—Flattened sphere.

*Bud color*.—143C, flattened apex (cluster of involucral bracts) 178A.

*Bud surface*.—Glabrous.

Peduncle:

*Peduncle shape*.—Terete with longitudinal ribs or ridges.

*Peduncle length* (*from uppermost leaf to base of calyx*).—7 cm-9 cm.

*Peduncle diameter*.—4.0 mm.

*Peduncle surface*.—Ridged, very faintly puberulent.

*Peduncle strength*.—Very strong and stiff.

*Peduncle color*.—145B between longitudinal ridges; ridge color 144B.

Peduncle bracts:

*Arrangement*.—One opposite pair attached to base of calyx-like cluster of involucral bracts.

*Attachment*.—Sessile.

*Shape*.—Lanceolate, contorted, and twisted.

*Margin*.—Smooth, entire.

*Apex*.—Acute.

*Base*.—Truncate.

*Color* (*both surfaces*).—137B.

*Dimensions*.—10-12 mm in length, 4-6 mm in width.

*Surface* (*both surfaces*).—Glabrous.

Ray florets:

*Ray floret arrangement*.—Whorled, two concentric whorls.

*Shape*.—Fan-like.

*Quantity*.—45-50 per inflorescence.

*Aspect*.—Initially upright, becoming horizontal when fully developed.

*Corolla tube dimensions*.—6 mm in length, 1.5 mm in diameter.

*Corolla tube color*.—Ranges between 145A and 145C.

*Ray floret corolla tube base*.—Truncate.

Ray floret petals:

*Shape*.—Fan-like: corolla tube subtends petals which divide into 3-5 linear free petal lobes.

*Surface* (*both surfaces*).—Glabrous.

*Dimensions*.—32-35 mm in length, 20 mm in width across all lobes.

*Lobe dimensions* (*free*).—15-22 mm in length, 2-3 mm in width at base of free lobe.

*Ray floret petal lobe apex*.—Predominantly acute, apex occasionally notched, depth of notch 1 mm-2 mm.

*Margin*.—Entire.

*Color* (*both surfaces*).—NN155D.

Involucral bracts:

*Quantity*.—45-50 per inflorescence, overlapping, fused at base.

*Bract shape*.—Lanceolate.

*Bract length*.—7-8 mm.

*Bract width*.—1-2 mm.

*Bract color* (*abaxial and adaxial surfaces*).—143C centrally, margins 151D.

*Bract margins*.—Ciliate, cilia tiny, color 178A.

*Bract apex*.—Rounded with tiny cilia, color 178A.

*Bract base* (*range*).—Rounded.

*Bract surface* (*both surfaces*).—Glabrous, translucent towards margin.

Disc floret:

*Disc diameter*.—26-28 mm.

*Disc floret quantity*.—Approximately 375-400 per inflorescence, massed at center of receptacle.

*Disc floret dimensions*.—7 mm in length, 1.5 mm in diameter.

*Disc floret shape*.—Tubular.

*Disc floret corolla tube*.—4 mm in length, 0.75 mm in diameter, color 145B-145C.

*Disc floret petal quantity*.—Ranges from 3 to 5 in number, basally fused.

*Disc floret petal dimensions*.—3 mm in length, 0.75 mm-1.0 mm in width.

*Disc floret petal color*.—14A.

*Disc floret petal apex*.—Acute.

*Disc floret petal base*.—Truncate.

Reproductive organs:

*Ray flowers*.—Stamens: 5 in number. Filaments: 2-3 mm in length, fine, color 1D. Anthers, pollen: Not present. Pistil: 1, 3 mm in length, forked and recurved, each branch 1.0-1.5 mm in length, fine, color 2B. Stigma, ovary: Not present.

*Disc flowers*.—Stamens: Quantity not determined, probably fused appearing as one, length 1 mm, color 175A. Anthers, pollen: None observed. Pistil: 1, less than 1 mm in length, stigma, style, ovary not observed.

Seed: None observed to date.

COMPARISON WITH PARENTAL LINES AND KNOWN VARIETY

Whereas 'Real Winner' exhibits a strong growth habit and profuse flowering with flowers consisting of pure white fringed ray florets, the female parent, seedling code L1028-8, bears simple (non-quilled, non-fringed) white ray florets, and the male parent, seedling code L1304-13, bears white quilled ray florets but lacks the plant vigor and profuse flowering of 'Real Winner'.

The commercial variety of *Leucanthemum* which the inventor considers most closely to resemble 'Real Winner' is the inventor's earlier variety of *Leucanthemum* Plant Named 'Real Galaxy' (U.S. Plant Pat. No. 23,873).

Both varieties 'Real Winner' and Real Galaxy' bear fine fringed white petals. However, the inventors consider that 'Real Winner' differs from, and is an improvement on, 'Real Galaxy' as follows:

1. Plants of 'Real Winner' are more compact, being approximately two-thirds the height and width of plants of 'Real Galaxy'.
2. The basal leaves of 'Real Winner' are approximately half the length (up to 125 mm in length) of the leaves of 'Real Galaxy' which can reach 200 mm in length.
3. The ray florets of 'Real Winner' are entirely pure white in color, whereas the ray florets of 'Real Galaxy' are off-white in color and exhibit yellow petal apices.
4. In periods of heavy rainfall, plants and flowers of 'Real Winner' hold up better and recover sooner than do plants of 'Real Galaxy'.

I claim:

1. A new and distinct cultivar of *Leucanthemum* Plant Named 'Real Winner' as described and illustrated herein.

* * * * *